US009012428B2

(12) United States Patent
Jonckers et al.

(10) Patent No.: US 9,012,428 B2
(45) Date of Patent: Apr. 21, 2015

(54) URACYL SPIROOXETANE NUCLEOSIDE PHOSPHORAMIDATES

(75) Inventors: Tim Hugo Maria Jonckers, Edegem (BE); Pierre Jean-Marie Bernard Raboisson, Rosieres (BE); Koen Vandyck, Paal-Beringen (BE); Steven Maurice Paula Van Hoof, Merelbeke (BE); Lili Hu, Mechelen (BE); Abdellah Tahri, Anderlecht (BE)

(73) Assignees: Janssen Products, LP, Horsham, PA (US); Medivir AB, Huddinge (SE)

( * ) Notice: Subject to any disclaimer, the term of this patent is extended or adjusted under 35 U.S.C. 154(b) by 2 days.

(21) Appl. No.: 13/884,852

(22) PCT Filed: Nov. 10, 2011

(86) PCT No.: PCT/EP2011/069865
§ 371 (c)(1),
(2), (4) Date: May 10, 2013

(87) PCT Pub. No.: WO2012/062870
PCT Pub. Date: May 18, 2012

(65) Prior Publication Data
US 2013/0244968 A1 Sep. 19, 2013

(30) Foreign Application Priority Data

Nov. 10, 2010 (EP) .................................... 10190660

(51) Int. Cl.
*A01N 43/04* (2006.01)
*A61K 31/70* (2006.01)
*A61K 9/28* (2006.01)
*C07H 19/06* (2006.01)
*C07H 19/10* (2006.01)
*A61K 9/20* (2006.01)

(52) U.S. Cl.
CPC .............. *C07H 19/10* (2013.01); *A61K 9/2866* (2013.01); *C07H 19/06* (2013.01); *A61K 9/2068* (2013.01); *A61K 9/284* (2013.01)

(58) Field of Classification Search
None
See application file for complete search history.

(56) References Cited

U.S. PATENT DOCUMENTS 8,481,519 B2    7/2013  Hoffmann et al.

FOREIGN PATENT DOCUMENTS

| WO | 2006012078 A2 | 2/2006 |
| WO | 2007020193 A2 | 2/2007 |
| WO | 2007095269 A2 | 8/2007 |
| WO | 2010130726 A1 | 11/2010 |

OTHER PUBLICATIONS

Babu et al, 2-Sprio ribo- and arabinonucleosides: synthesis, molecular modelling and incorporation into oligodeoxynucleotides, Organic & Biomolecular Chemistry, Sep. 12, 2003, p. 3514-3526, vol. 1(20).
Hecker, et al., Prodrugs of Phosphates and Phosphonates, J. Med. Chem., 2008, pp. 2328-2345, vol. 51.
Krieger, et al, Enhancement of Hepatitis C Virus RNA Replication by Cell Culture, Journal of Virology, May 1, 2001, 4614-1624, 75-10, DE.
Li, et al., Efficient Synthesis of Methyl 3,5-Di-O-Benzyl-a-D-Ribofuranoside and Application to the Synthesis of 2'-CB-Alkoxymethyluridines, Organic Letters, 2007, pp. 3009-3012, vol. 9, No. 16.
Lohmann, et al., Replication of Subgenomic Hepatitis C Virus RNAs in a Hepatoma Cell Line, Science, 1999, pp. 110-113, vol. 285.
U.S. Appl. No. 13/884,835, filed May 10, 2013, Tim Hugo Maria Jonckers.
U.S. Appl. No. 13/836,465, filed Mar. 15, 2013, Tim Hugo Maria Jonckers.
Hirokazu Awano, et al., "Synthesis and Antiviral Activity of 5-Substituted (2's)-2'-Deoxy-2'-C-Methylcytidines and—uridines", Arch. Pharm. Pharm. Med. Chem., 329, 1996, pp. 66-72.
L. W. Brox, et al., "Studies on the Growth Inhibition and Metabolism of 2'-Deoxy-2'-fluorocytidine in Cultured Human Lymphoblasts", Cancer Research, vol. 34., 1974, pp. 1838-1842.
M. A. Ivanov, et al., "Synthesis and Biological Properties of Pyrimidine 4'-Fluoronucleosides and 4'-Fluorouridine 5'-O-Triphosphate", Russian Journal of Bioorganic Chemistry, vol. 36, No. 4, 2010, pp. 488-496.
Lars Petter Jordheim, et al., "Advances in the Development of Nucleoside and Nucleotide Analogues for Cancer and Viral Diseases", Nature Reviews, Drug Discovery, vol. 12, 2013, pp. 447-464.
Klaus Klumpp, et al., "2'-Deoxy-4'-azido Nucleoside Analogs Are Highly Potent Inhibitors of Hepatitis C Virus Replication Despite the Lack of 2'-α-Hydroxyl Groups", The Journal of Biological Chemistry, vol. 283, No. 4, 2008, pp. 2167-2175.
Peng Liu, et al., "Fluorinated Nucleosides: Synthesis and Biological Implication", J Fluor Chem., 129 (9), 2008, pp. 743-766.
Akira Matsuda, et al., Radical Deoxygenation of *Tert*-Alcohols in 2'-Branched-Chain Sugar Pyrimidine Nucleosides: Synthesis and Antileukemic Activity of 2'-Deoxy-2' (*S*)-Methylcytidine[1], Chem. Pharm. Bull., vol. 35, No. 9, 1987, pp. 3967-3970.
Eisuke Murakami, et al., "Mechanism of Activation of β-D-2'-Deoxy-2'-Fluoro-2'-C-Methylcytidine and Inhibition of Hepatitis C Virus NS5B RNA Polymerase", Antimicrobial Agents and Chemotherapy, vol. 51, No. 2, 2007, pp. 503-509.
Michael J. Sofia, et al., "Discovery of a β-D-2'-Deoxy-2'-α-fluoro-2'-β-C-methyluridine Nucleotide Prodrug (PSI-7977) for the Treatment of Hepatitis C Virus", Journal of Medicinal Chemistry, vol. 53, No. 2010, pp. 7202-7218.
Michael J. Sofia, et al., "Nucleoside, Nucleotide, and Non-Nucleoside Inhibitors of Hepatitis C Virus NS5B RNA-Dependent RNA-Polymerase", Journal of Medicinal Chemistry, vol. 55, 2012, pp. 2481-2531.

*Primary Examiner* — Patrick Lewis

(57) ABSTRACT

This invention relates to a stereochemically pure uracyl spirooxetane nucleoside phosphoramidate useful in the treatment of patients infected with the hepatitis C virus (HCV).

9 Claims, No Drawings

URACYL SPIROOXETANE NUCLEOSIDE PHOSPHORAMIDATES

This application is a national stage application of PCT/EP2011/069865, filed Nov. 10, 2011, which claims priority benefit of Application No. EP 10190660.0 filed Nov. 10, 2010. The complete disclosures of the aforementioned related patent applications are hereby incorporated herein by reference for all purposes.

BACKGROUND OF THE INVENTION

This invention relates to an uracyl spirooxetane nucleoside phosphoramidate useful in the treatment of patients infected with the hepatitis C virus (HCV).

HCV is a single stranded, positive-sense RNA virus belonging to the Flaviviridae family of viruses in the hepacivirus genus. The NS5B region of the RNA polygene encodes a RNA dependent RNA polymerase (RdRp), which is essential to viral replication. Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations. There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapy is based on (pegylated) interferon-alpha (IFN-α) in combination with ribavirin. This combination therapy yields a sustained virologic response in more than 40% of patients infected by genotype 1 HCV and about 80% of those infected by genotypes 2 and 3. Beside the limited efficacy against HCV genotype 1, this combination therapy has significant side effects and is poorly tolerated in many patients. Major side effects include influenza-like symptoms, hematologic abnormalities, and neuropsychiatric symptoms. Hence there is a need for more effective, convenient and better-tolerated treatments.

Experience with HIV drugs, in particular with HIV protease inhibitors, has taught that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design.

The NS5B RdRp is essential for replication of the single-stranded, positive sense, HCV RNA genome. This enzyme has elicited significant interest among medicinal chemists. Both nucleoside and non-nucleoside inhibitors of NS5B are known. Nucleoside inhibitors can act as a chain terminator or as a competitive inhibitor, or as both. In order to be active, nucleoside inhibitors have to be taken up by the cell and converted in vivo to a triphosphate. This conversion to the triphosphate is commonly mediated by cellular kinases, which imparts additional structural requirements on a potential nucleoside polymerase inhibitor. In addition this limits the direct evaluation of nucleosides as inhibitors of HCV replication to cell-based assays capable of in situ phosphorylation.

Several attempts have been made to develop nucleosides as inhibitors of HCV RdRp, none have proceeded all the way to registration. Amongst the problems which HCV-targeted nucleosides have encountered to date are toxicity, mutagenicity, lack of selectivity, poor efficacy, poor bioavailability, sub-optimal dosage regimes and ensuing high pill burden, and cost of goods.

There is a need for HCV inhibitors that may overcome the disadvantages of current HCV therapy such as side effects, limited efficacy, the emerging of resistance, and compliance failures, as well as improve the sustained viral response.

The present invention concerns butyl N—[(S)-{[(4R,5R,7R,8R)-5-(2,4-dioxo-3,4-di-hydropyrimidin-1(2H)-yl)-8-hydroxy-1,6-dioxaspiro[3.4]oct-7-yl]methoxy}(phenoxy)-phosphoryl]-L-alaninate having useful antiviral properties. Spirooxetane nucleosides, in particular 1-(2-O,2-C-ethano-β-D-ribofuranosyl)thymine and 1-(2-O,2-C-ethano-β-D-ribofuranosyl)uracil have been described in Org. Biomol. Chem., 2003, 3514-3526. These compounds were tested against HIV, but no activity was found.

The compound of the invention may also be attractive due to the fact that it lacks activity against other viruses, in particular against HIV. HIV-infected patients often suffer from co-infections such as HCV. Treatment of such patients with an HCV inhibitor that also inhibits HIV may lead to the emergence of resistant HIV strains.

DESCRIPTION OF THE INVENTION

In one aspect, the present invention provides for butyl N—[(S)-{[(4R,5R,7R,8R)-5-(2,4-dioxo-3,4-dihydropyrimidin-1(2H)-yl)-8-hydroxy-1,6-dioxaspiro[3.4]oct-7-yl]methoxy}(phenoxy)phosphoryl]-L-alaninate and the pharmaceutically acceptable salts and solvates thereof. This compound is represented by the formula I:

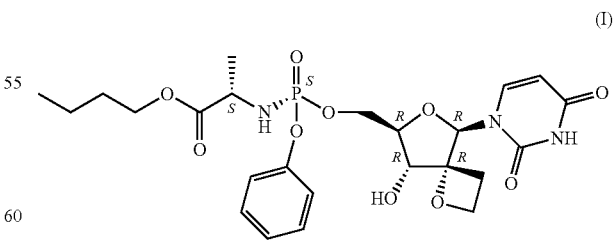

(I)

Whenever used herein, the term "compound of formula I", "the present compound", "compound of the present invention", it is meant to include the compound of formula I as well as the pharmaceutically acceptable salts and solvates thereof, unless specified differently.

The IUPAC name in this description for the compound of formula (I) has been generated by commercial ACD/Labs NAME software version 12.

In a further aspect, the invention concerns the use of the compound of formula I as a medicine, more in particular, for inhibiting HCV. Suitably, the present invention concerns a compound of formula I for use in the treatment or prophylaxis of HCV infection. Alternatively, there is provided the use of a compound of formula I for the manufacture of a medicament for inhibiting HCV. Suitably the present invention concerns the use of a compound of formula I for the manufacture of a medicament for the treatment or prophylaxis of HCV infection.

Representative HCV genotypes in the context of treatment or prophylaxis in accordance with the invention include genotype 1b (prevalent in Europe) or 1a (prevalent in North America). The invention also provides a method for the treatment or prophylaxis of HCV infection, in particular of the genotype 1a or 1b.

The compound of formula (I) is a pure stereoisomeric form. A pure stereoisomeric form as mentioned herein is defined as a stereoisomer substantially free of other enantiomeric or diastereomeric forms of the same basic molecular structure of the compound of formula (I). In particular, a pure stereoisomeric form concerns a compound having a stereoisomeric excess of at least 80% (i.e. minimum 90% of one isomer and maximum 10% of the other possible isomers) up to a stereoisomeric excess of 100% (i.e. 100% of one isomer and none of the other), more in particular, a compound having a stereoisomeric excess of 90% up to 100%, even more in particular having a stereoisomeric excess of 94% up to 100% and most in particular having a stereoisomeric excess of 97% up to 100%, or of 98% up to 100%. The terms "enantiomerically pure" and "diastereomerically pure" should be understood in a similar way, but then having regard to the enantiomeric excess, and the diastereomeric excess, respectively, of the mixture in question.

The pure stereoisomeric form of the present compound may be obtained by separation techniques or by stereospecific synthesis procedures using pure stereochemically isomeric forms of the appropriate starting materials. For instance, enantiomers may be separated from each other by the selective crystallization of their diastereomeric salts with optically active acids or bases. Examples thereof are tartaric acid, dibenzoyl-tartaric acid, ditoluoyltartaric acid and camphorsulfonic acid. Alternatively, enantiomers may be separated by chromatographic techniques using chiral stationary layers or by using super critical fluid chromatography.

The pharmaceutically acceptable addition salts comprise the therapeutically active non-toxic acid or base addition salt forms of the compound of formula I. Of interest is the free, i.e. non-salt form, of the compound of formula I.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The pharmaceutically acceptable base addition salts, such as metal or amine salt forms, can conveniently be obtained by treating the acid form with an appropriate organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvate that the compound of formula I, as well as the salts thereof, is able to form. Such solvates are for example hydrates, alcoholates, e.g. ethanolates, propanolates, and the like.

The present invention also includes an isotope-labeled compound of formula I wherein one or more of the atoms is replaced by an isotope that differs from the one(s) typically found in nature. Examples of such isotopes include isotopes of hydrogen, such as $^2$H and $^3$H; carbon, such as $^{11}$C, $^{13}$C and $^{14}$C; nitrogen, such as $^{13}$N and $^{15}$N; oxygen, such as $^{15}$O, $^{17}$O and $^{18}$O; phosphorus, such as $^{31}$P and $^{32}$P. An isotope-labeled compound of the invention can be prepared by processes analogous to those described herein by using the appropriate isotope-labeled reagents or starting materials, or by art-known techniques. The choice of the isotope included in an isotope-labeled compound depends on the specific application of that compound. For example, for tissue distribution assays, a radioactive isotope such as $^3$H or $^{14}$C is incorporated. For radio-imaging applications, a positron emitting isotope such as $^{11}$C, $^{18}$F, $^{13}$N or $^{15}$O will be useful. The incorporation of deuterium may provide greater metabolic stability, resulting in, e.g. an increased in vivo half life of the compound or reduced dosage requirements.

In a further aspect, the present invention concerns a pharmaceutical composition comprising a therapeutically effective amount of a compound of formula I as specified herein, and a pharmaceutically acceptable carrier. Said composition may contain from 1% to 50%, or from 10% to 40% of a compound of formula I and the remainder of the composition is the said carrier. A therapeutically effective amount in this context is an amount sufficient (i) to act in a prophylactic way against HCV infection, or (ii) to inhibit HCV replication, or (iii) to stabilize HCV infection, or (iv) to reduce HCV infection, or (v) to eradicate HCV infection, in infected subjects or subjects being at risk of becoming infected. In still a further aspect, this invention relates to a process of preparing a pharmaceutical composition, which comprises intimately mixing a pharmaceutically acceptable carrier with a therapeutically effective amount of a compound of formula I.

The compound of formula I may be formulated into various pharmaceutical forms for administration purposes. As appropriate compositions there may be cited all compositions usually employed for systemically administering drugs. To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compound of formula I is active against HCV and can be used in the treatment and or prophylaxis of HCV infection or diseases associated with HCV. The latter include progressive liver fibrosis, inflammation and necrosis leading to cirrhosis, end-stage liver disease, and HCC. The compound of this invention is believed to be active against mutated strains of HCV, and has a favorable pharmacokinetic profile. It further has attractive properties in terms of bioavailability, including an acceptable half-life, AUC (area under the curve) and peak values.

The in vitro antiviral activity against HCV of the compound of formula I was tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to its anti-HCV properties, the compound of formula I, including the pharmaceutically acceptable addition salts or solvates thereof, are useful in the treatment of warm-blooded animals, in particular humans, infected with HCV, and in the prophylaxis of HCV infections. The compounds of the present invention may therefore be used as a medicine, in particular as an anti-HCV or a HCV-inhibiting medicine. The present invention also relates to the use of the present compounds in the manufacture of a medicament for the treatment or the prevention of HCV infection. In a further aspect, the present invention relates to a method of treating a warm-blooded animal, in particular human, infected by HCV, or being at risk of becoming infected by HCV, said method comprising the administration of an anti-HCV effective amount of a compound of formula I. Said use as a medicine or method of treatment comprises the systemic administration to HCV-infected subjects or to subjects susceptible to HCV infection of an amount effective to combat or prevent the conditions associated with HCV infection.

When administered to a human, in particular a patient, the compound of the present invention is a prodrug of the phosphoramidate type. It acts as a precursor to its monophosphate ester derivative, which can then be further phosphorylated to the tri-phosphate ester. According to in Hecker, S. et al. J. Med. Chem. 2008, Vol 51(8) p 2328, the cleavage of this type of prodrug is initiated by an esterase. A carboxylate intermediate is liberated which is believed to cyclize intramolecularly to give a five membered intermediate by which an aryloxy moiety is liberated. The five-membered intermediate formed is then hydrolyzed to form a phosphoramidic acid. Finally this monoamidate is further hydrolyzed (possibly catalyzed by a second enzyme (phosphoramidase) to give the nucleoside monophosphate.

In general it is contemplated that an antiviral effective daily amount would be from about 1 to about 200 mg/kg, or about 5 to about 175 mg/kg, or about 10 to about 150 mg/kg, or about 20 to about 100 mg/kg, or about 50 to about 75 mg/kg body weight. Average daily doses can be obtained by multiplying these daily amounts by about 70. It may be appropriate to administer the required dose as two, three, four or more sub-doses at appropriate intervals throughout the day. Said sub-doses may be formulated as unit dosage forms, for example, containing about 1 to about 5000 mg, or about 50 to about 3000 mg, or about 100 to about 1000 mg, or about 200 to about 600 mg, or about 100 to about 400 mg of active ingredient per unit dosage form.

As used herein the term "about" has the meaning known to the person skilled in the art. In certain embodiments the term "about" may be left out and the exact amount is meant. In other embodiments the term "about" means that the numerical following the term "about" is in the range of ±15%, or of ±10%, or of ±5%, or of ±1%, of said numerical value.

Methods Used in the Examples

LC-MS analysis was done using either one of the following methods.

HPLC Condition A

System: Waters Alliance 2695

Column: Waters XTerra 2.5 µm 4.6×50 mm; Column temp.: 55° C.; Flow: 2 mL/min

Mobile phase A: 10 mM ammonium acetate+0.1% HCOOH in $H_2O$

Mobile phase B: $CH_3CN$

| Time | % A | % B |
|---|---|---|
| 0.00 | 85 | 15 |
| 3.00 | 5 | 95 |
| 4.20 | 5 | 95 |
| 4.30 | 85 | 15 |
| 5.40 | 85 | 15 |

HPLC Condition B

System: Waters Alliance 2695

Column: Hypercarb 3μ 4.6×50 mm; Column temp.: 50° C.; Flow: 2 mL/min

Mobile phase A: 10 mM ammonium acetate in $H_2O/CH_3CN$ 1/9

Mobile phase B: 10 mM ammonium acetate in $H_2O/CH_3CN$ 9/1

| Time | % A | % B |
|---|---|---|
| 0.00 | 0 | 100 |
| 3.00 | 100 | 0 |
| 4.20 | 100 | 0 |
| 4.30 | 0 | 100 |
| 5.40 | 0 | 100 |

The NMR spectra were recorded on a Bruker 400 spectrometer, operating at 400 MHz for $^1$H. Chemical shifts are given in ppm and a J values in Hz. Multiplicity is indicated using the following abbreviations: d for doublet, t for a triplet, m for a multiplet

EXAMPLES

The compound of formula (I) was prepared according to synthesis scheme 3 and involves the reaction of 1-[(4R,5R,7R,8R)-8-hydroxy-7-(hydroxymethyl)-1,6-dioxaspiro[3.4]oct-5-yl]pyrimidine-2,4(1H,3H)-dione (intermediate 10), prepared according to synthesis scheme 1, and (2S)-butyl 2-(chloro(phenoxy)phosphorylamino)-propanoate (intermediate 12), prepared according to synthesis scheme 2.

Scheme 1: Synthesis of intermediate 10

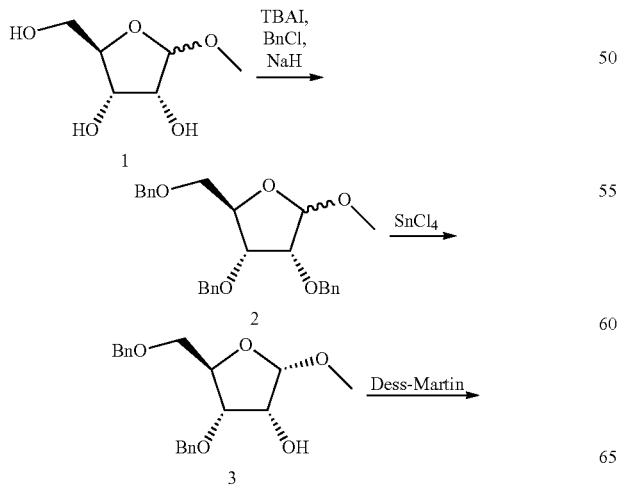

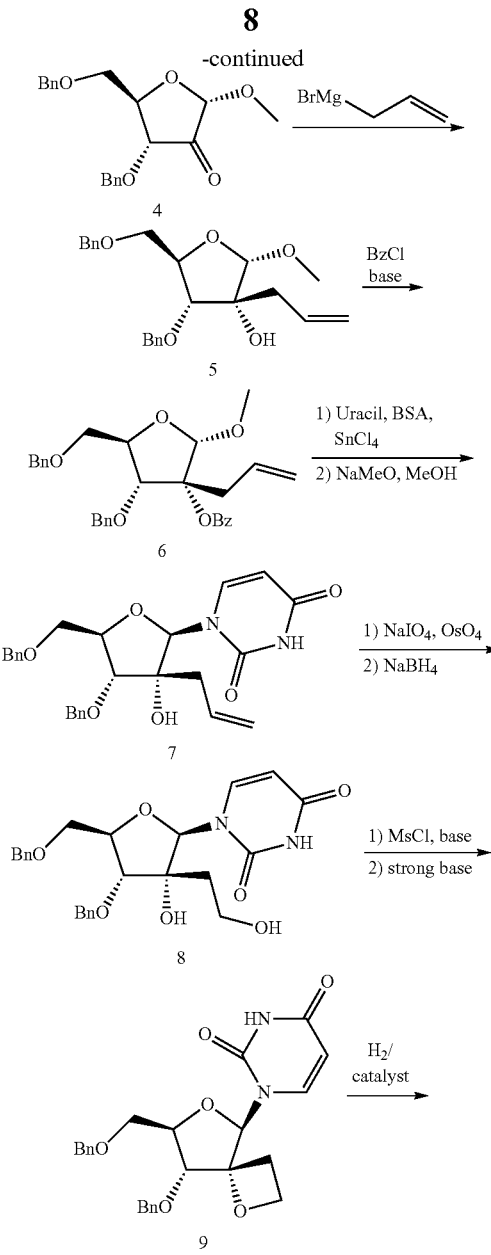

Example 1

Synthesis of intermediate (2S,3R,4R,5R)-3-allyl-4-(benzyloxy)-5-(benzyl-oxymethyl)-2-methoxytetrahydrofuran-3-ol (5)

Under argon atmosphere, to a solution of 4 (which can be prepared according to the procedures described in Org. Lett., 2007, 9, 3009-3012) in dry tetrahydrofurane (THF; 400 mL) at −78° C., allylmagnesium bromide (400 mL, 400 mmol; 1.0 M in diethylether) was added. After stirring the reaction mixture at −78° C. for 4 hours, the reaction mixture was allowed to stir at room temperature for 2 hours. The reaction was carefully quenched with saturated aqueous ammonium chloride. The mixture was extracted with dichloromethane, and the organic layer was washed with brine. The solvent was removed, and the residue was purified by silica gel chromatography (600 g silica), by gradient elution with 15% to 20% ethyl acetate in hexane to give the reaction product 5 as a colorless oil (32.9 g, 70%).

HPLC Condition A, Rt: 2.97 min, m/z=402 (M+NH$_4$)$^+$. $^1$H NMR (400 MHz, CDCl$_3$) δ ppm 7.38-7.20 (m, 10H), 5.84-5.97 (m, 1H), 5.12 (d, 1H, J=10.2 Hz), 5.01 (d, 1H, J=17.2 Hz), 4.74 (d, 1H, J=12.3 Hz), 4.56 (s, 1H), 4.53-4.40 (m, 3H), 4.05-4.11 (m, 1H), 3.32-3.53 (m, 4H), 3.44 (s, 3H), 2.37 (dd, 1H, J=14.3, 6.7 Hz), 2.25 (dd, 1H, J=14.3, 7.6 Hz).

Example 2

Synthesis of intermediate (2S,3R,4R,5R)-3-allyl-4-(benzyloxy)-5-(benzyl-oxymethyl)-2-methoxytetrahydrofuran-3-yl benzoate (6)

To a solution of 5 (26.6 g, 69.2 mmol) in dry dichloromethane (500 mL) at room temperature, N,N-dimethylpyridin-4-amine (DMAP; 2.113 g, 17.30 mmol), triethyl-amine (217 mL, 1557 mmol) and benzoyl chloride (18.05 mL, 156 mmol) were added. After 1 hour, additional benzoyl chloride (6 mL) and DMAP (2.1 g) were added. The mixture was stirred for 5 days.

The reaction mixture was then stirred with 1 N HCl and extracted with dichloro-methane. The organic layers were combined and washed with saturated aqueous NaHCO$_3$ followed by brine. After drying with MgSO$_4$, filtration and evaporation of the volatiles, the residue was purified by column chromatography (400 g silica) eluting with heptane to 15% ethyl acetate in heptane to give reaction product as an oil (as a mixture with compound 5). The mixture was purified again with CH$_2$Cl$_2$ as eluent (400 g silica). The pure fractions were collected and intermediate 6 was obtained as a colorless oil (13.05 g, 39%). HPLC Condition A, Rt: 3.41 min, m/z=457 (M-OMe)$^+$. $^1$H NMR (400 MHz, CDCl$_3$) δ ppm 8.1 (d, 2H, J=7.9 Hz), 7.68-7.28 (m, 13H), 5.84-5.77 (m, 1H), 5.12 (d, 1H, J=16 Hz), 4.95 (d, 1H, J=16 Hz), 4.92 (d, 1H, J=12.3 Hz), 4.56 (d, 1H, J=12.3 Hz), 4.48 (d, 1H, J=11.6 Hz), 4.40 (d, 1H, J=11.6 Hz), 4.2 (m, 1H), 3.85 (d, 1H, J=6.2 Hz), 3.53 (d, 1H, J=10.8 Hz), 3.7 (s, 3H), 3.45 (dd, 1H, J=10.8, 6.2 Hz), 3.25 (dd, 1H, J=15.5, 7.3 Hz), 2.45 (dd, 1H, J=15.5, 7.3 Hz).

Example 3

Synthesis of intermediate 1-[(2R,3R,4R,5R)-3-allyl-4-(benzyloxy)-5-(benzyloxymethyl)-3-hydroxytetrahydrofuran-2-yl]pyrimidine-2,4(1H,3H)-dione (7)

Bis(trimethylsilyl)acetamide (BSA; 29.2 mL, 118 mmol) was added to a mixture of 6 (14.0 g, 23.1 mmol) and uracil (5.99 g, 53.4 mmol) in anhydrous acetonitrile (300 mL). The reaction mixture was refluxed for 1 hour and the clear solution was allowed to cool down to room temperature. Tinchloride (11.55 mL, 99 mmol) was added dropwise at room temperature and the mixture was further stirred for 1 hour. The mixture was then stirred at reflux for 1.5 hour and again cooled to room temperature. Ethyl acetate (250 mL) was added, followed by saturated aqueous NaHCO$_3$ (250 mL) and the mixture was stirred for 15 minutes. After filtration through Celite, the organic layer was separated and washed with saturated aqueous NaHCO$_3$ (250 mL). The combined aqueous layer was extracted with ethyl acetate (250 mL) and the combined organic layer was dried (MgSO$_4$), filtered and evaporated to dryness under reduced pressure. The resulting yellow oil was dissolved in methanol and 25% sodium methanolate (25 mL) was added. Stirring continued overnight. More 25% sodium methanolate (15 mL) was added and stirring was continued overnight. Acetic acid (30 mL) was added and the solvent was removed. The residue was purified by column chromategraphy with heptane/ethyl acetate 50:50 to 100% ethyl acetate. Intermediate 7 (9.38 g, 76%) was obtained as a colorless oil. HPLC Condition A, Rt: 2.49 min, m/z=465 (M+H)$^+$. $^1$H NMR (400 MHz, CDCl$_3$) δ ppm 8.39 (1H, NH), 7.75 (d, 1H, J=8.0 Hz), 7.22-7.43 (m, 10H), 6.05 (s, 1H), 5.71-5.84 (m, 1H), 5.35 (d, 1H, J=8.0 Hz), 5.00-5.11 (m, 2H), 4.70 (d, 1H, J=11.5 Hz), 4.53 (d, 1H, J=11.5 Hz), 4.47 (d, 1H, J=11.1 Hz), 4.47 (d, 1H, J=11.1 Hz), 4.11-4.16 (m, 1H), 4.04 (d, 1H, J=8.0 Hz), 3.81-3.87 (m, 1H), 3.45-3.52 (m, 1H), 3.17 (bs, OH), 2.15-2.33 (m, 2H).

Example 4

Synthesis of intermediate 1-[(2R,3R,4R,5R)-4-(benzyloxy)-5-(benzyl-oxymethyl)-3-hydroxy-3-(2-hydroxyethyl)tetrahydrofuran-2-yl]pyrimidine-2,4(1H, 3H)-dione (8)

To a stirred solution of 7 (7.8 g, 16.79 mmol) in a mixture of THF (10 mL) and H$_2$O (10 mL) was added sodium periodate (11.17 g, 52.2 mmol) followed by osmium(VIII) tetroxide (2 mL, 2.5 w/v % in tert-Butanol, 0.168 mmol) and stirring was continued for 2 hour at room temperature. Water (100 mL) was added and extraction was performed with ethyl acetate (2×50 mL). The organic layer was washed with saturated aqueous NaHCO$_3$ (2×30 mL). The combined aqueous layer was extracted with ethyl acetate and the combined organic layer was dried over (Na$_2$SO$_4$), filtered and evaporated to dryness under reduced pressure. The oily residue obtained was dissolved in a mixture of THF (100 mL) and H$_2$O (20 mL) and sodium borohydride (1.361 g, 36.0 mmol) was added. The reaction mixture was stirred overnight at room temperature, whereupon water (100 mL) was added and extraction was performed with ethyl acetate (2×50 mL). The combined organic layer was washed with saturated aqueous NaHCO$_3$, the combined aqueous layer was extracted with ethyl acetate, and the combined organic layer was dried over (Na$_2$SO$_4$), filtered and evaporated to dryness under reduced pressure. The oily residue obtained was purified by column chromatography (0-10% (v/v) methanol in CH$_2$Cl$_2$ then 10% isocratic) affording reaction product 8 as a white foam (4.8 g, 57%). HPLC Condition A, Rt: 2.12 min, m/z=469 (M+H)$^+$. $^1$H NMR (400 MHz, CDCl$_3$) δ ppm 9.85 (1H, NH), 7.85 (d, 1H, J=8.0 Hz), 7.22-7.43 (m, 10H), 6.05 (s, 1H), 5.35 (d, 1H, J=8.0 Hz), 4.75 (d, 1H, J=11.5 Hz), 4.53 (d, 1H, J=11.5 Hz), 4.45 (d, 1H, J=11.3 Hz), 4.35 (d, 1H, J=11.3 Hz), 4.27 (d, 1H, J=6.6 Hz), 4.2 (s, 1H), 4.1, (d, 1H, J=6.6 Hz), 3.95 (d, 1H, J=10.8 Hz), 3.75-3.7 (m, 1H), 3.62 (d, 1H, J=10.8 Hz), 3.17 (bs, OH), 1.8-1.7 (m, 2H).

Example 5

Synthesis of intermediate 1-[(4R,5R,7R,8R)-8-(benzyloxy)-7-(benzyloxy-methyl)-1,6-dioxaspiro[3.4]octan-5-yl]pyrimidine-2,4(1H,3H)-dione (9)

Methanesulfonyl chloride (0.800 mL, 10.34 mmol) was added to 8 (4.32 g, 9.22 mmol) in dry pyridine (100 mL).

After 1 hour and 15 minutes, 0.1 equivalents more methanesulfonyl chloride was added and the mixture was further stirred at room temperature for 45 minutes. Then, a small amount of methanol was added and the mixture was evaporated to dryness. The residue was dissolved in ethyl acetate (100 mL) and washed with saturated NaHCO$_3$ (2×50 mL). The combined aqueous layer was extracted with ethyl acetate. The combined organic layer was then dried over Na$_2$SO$_4$ and concentrated in vacuo. The obtained residue was dissolved in dry THF and 95% NaH (932 mg, 36.9 mmol) was added at once at room temperature. After stirring for 2 hours at room temperature, the reaction mixture was poured on a saturated aqueous solution of NH$_4$Cl (30 mL) followed by addition of CH$_2$Cl$_2$ (250 mL). The separated organic layer was washed with saturated aqueous NaHCO$_3$ (2×100 mL) and the combined aqueous layer was extracted with CH$_2$Cl$_2$ (250 mL). The combined organic layer was dried (Na$_2$SO$_4$), filtered and evaporated to dryness under reduced pressure. The residue obtained was purified by column chromatography eluting first with heptane, then with ethyl acetate to afford 9 (3.27 g, 79%) as a foam. HPLC Condition A, Rt: 2.33 min, m/z=451 (M+H)$^+$. $^1$H NMR (400 MHz, CDCl$_3$) δ ppm 2.20-2.38 (m, 1 H) 2.38-2.52 (m, 1 H) 3.62-3.73 (m, 1 H) 3.89-4.13 (m, 3 H) 4.38-4.56 (m, 3 H) 4.56-4.68 (m, 1 H) 4.70-4.88 (m, 2 H) 5.25 (d, J=8.00 Hz, 1 H) 6.25 (s, 1 H) 7.18-7.47 (m, 10 H) 7.87 (d, J=8.20 Hz, 1 H) 8.90 (br. s., 1 H)

Example 6

Synthesis of intermediate 1-[(4R,5R,7R,8R)-8-hydroxy-7-(hydroxyl-methyl)-1,6-dioxaspiro[3.4]octan-5-yl]pyrimidine-2,4(1H,3H)-dione (10)

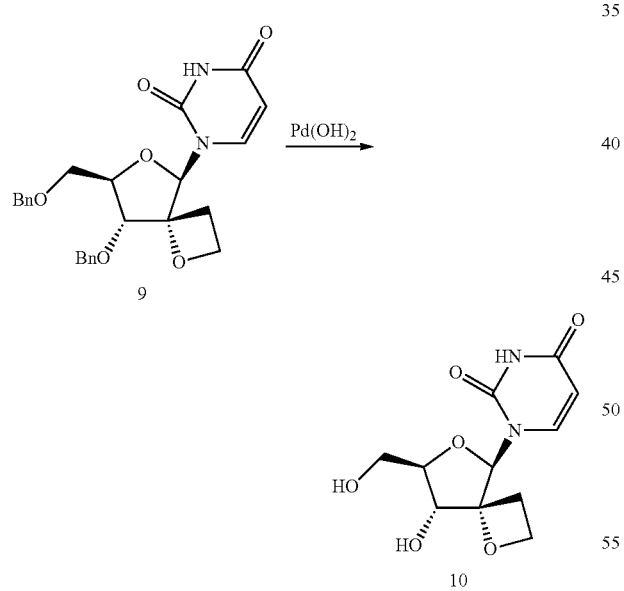

A mixture of 9 (50 mg, 0.111 mmol) in methanol (1 mL) and Pd(OH)$_2$ (8 mg) was stirred under a hydrogen atmosphere at room temperature. After 4 hours, more Pd(OH)$_2$ (30 mg) and methanol (1 mL) were added. The mixture was stirred vigorously under H$_2$-atmosphere overnight. The catalyst was removed by filtration over decalite, and the solvent was removed by evaporation. The resulting residue was purified by silica gel chromatography eluted with 10% methanol in ethyl acetate to give the intermediate 10 as white powder (16.8 mg; 56%). HPLC Condition B, Rt: 1.98 min, m/z=271 (M+H)$^+$. $^1$H NMR (400 MHz, D$_2$O) δ ppm 7.65 (d, 1H, J=8.0 Hz), 6.11 (s, 1H), 5.82 (d, 1H, J=8.0 Hz), 4.46-4.61 (m, 2H), 4.06-4.13 (m, 1H), 3.87-3.95 (m, 1H), 3.69-3.77 (m, 2H), 2.62-2.73 (m, 1H), 2.48-2.58 (m, 1H).

Scheme 2: Synthesis of intermediate 12

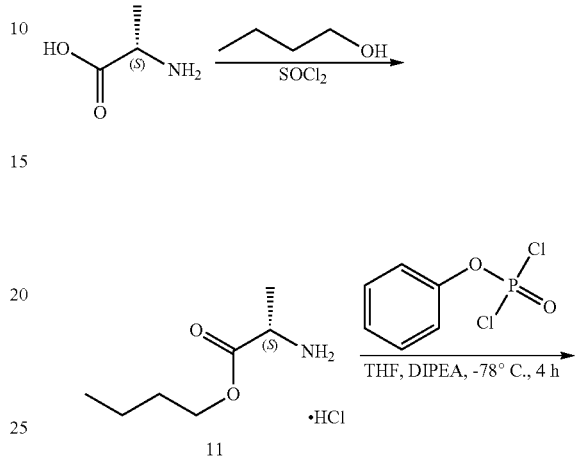

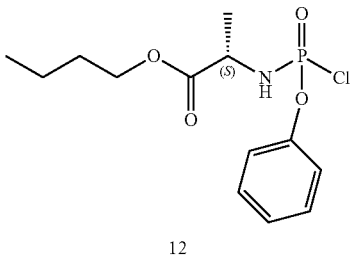

Example 7

Synthesis of intermediate (2S)-butyl 2-(chloro(phenoxy)phosphorylamino)-propanoate (12)

1-Butanol (1200 mL) was cooled to −20° C. and 50 mL of SOCl$_2$ added with stirring followed by 50 g (33.67 mmol) of (S)-2-aminopropanoic acid. The solution was heated 24 hrs at reflux, most of the solvent stripped off, and the residue was dissolved in 800 mL of diethyl ether. The mixture was left for 1 hr at 0° C. to afford (S)-butyl 2-aminopropanoate hydrochloride (intermediate 11.47 g). Phenyl phosphorodichloridate (48.9 g, 232 mmol) and (S)-butyl 2-aminopropanoate hydrochloride (42 g, 232 mmol) were suspended in anhydrous CH$_2$Cl$_2$ (200 mL). N,N-diisopropylethylamine (59.9 g, 464 mmol) was added drop wise at −78° C., and after 4 hrs the reaction was concentrated. Diethylether (Et$_2$O, 500 mL) was added and the resulting precipitate was filtered off and washed with dry Et$_2$O (twice 100 mL). The filtrate was evaporated to dryness. (2S)-butyl 2-(chloro(phenoxy)phosphorylamino)propanoate (12) was stored as 0.5 M solution in THF at −18° C. until further reaction.

Scheme 3: synthesis of compound P1

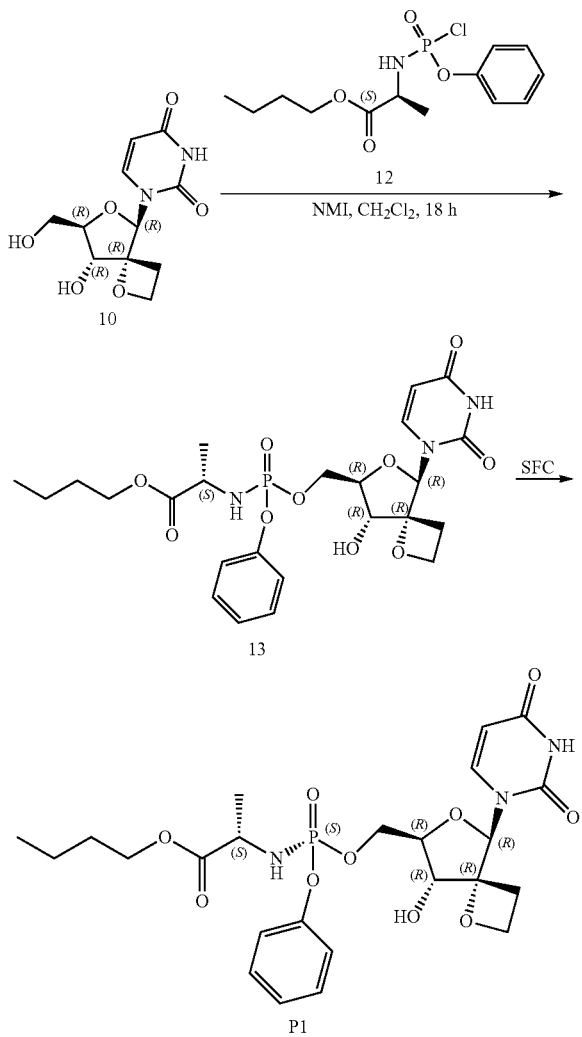

Example 8

Synthesis of Intermediate 13

To a solution of 10 (12 g, 44.4 mmol) in 480 mL dry CH$_2$Cl$_2$ was added 1-methyl-imidazole (43.74 g, 532 mmol) at 25° C. A solution of 12 (120 mL, 0.5 M in THF) was added drop wise and the mixture was stirred at 25° C. for 18 hrs. Another 120 mL of 12 (0.5 M in THF) was added dropwise. The resulting mixture was stirred for 5 hrs. The reaction mixture was quenched with 20 mL of water. The resulting mixture was concentrated.

Example 9

Preparation of butyl N—[(S)-{[(4R,5R,7R,8R)-5-(2,4-dioxo-3,4-dihydro-pyrimidin-1(2H)-yl)-8-hydroxy-1,6-dioxaspiro[3.4]oct-7-yl]methoxy}(phenoxy)-phosphoryl]-L-alaninate (compound P1)

The residue resulting from example 8 was purified by column chromatography on silica gel (CH$_2$Cl$_2$/methanol=30/1) yielding 3 fractions: 1) 4 g, 96% pure (purity based on LC-MS), 2) 7 g, 80% pure and 3) 3.5 g with a purity of less than 80%. The impure fractions (with purity <95%) were combined and purified again by column chromatography on silica gel (from CH$_2$Cl$_2$ to CH$_2$Cl$_2$/methanol=50/1) to obtain an additional fraction of 3.1 g with a purity of at least 95%. In total 7.1 g with a purity of at least 95% was obtained. 1.3 g thereof was purified by supercritical fluid chromatography (SFC) on a Multigram™II Supercritical Fluid Chromatography system from Berger instruments (Newark, Del., USA), using a Chiralpak Diacel OJ 20×250 mm column.

Purification was done at room temperature, using a nozzle pressure of 100 bar and a flow rate of 50 mL/min. The mobile phase used was CO$_2$, ethanol with 0.2% isopropylamine. 544 mg of 100% pure P1 was obtained as a white solid.

The retention time for compound P1 was as follows: R$_t$ (SFC): 6.68 min.

LC-MS analysis in this example was done using the following conditions: Column: SunFire C18 3.5μ 4.6×100 mm, mobile phase A: 10 mM NH$_4$OOCH+0.1% HCOOH in H$_2$O, mobile phase B: methanol operating at a column temperature of 50° C. using a flow rate of 1.5 mL/min. Gradient conditions: t=0 min: 65% A, 35% B; t=7 min, 5% A, 95% B; t=9.6 min, 5% A, 95% B; t=9.8 min: 65% A, 35% B; t=12 min, 65% A, 35% B. For P1 the following data were found: R$_t$(LC-MS): 4.79 min, m/z=554 (M+H)+

NMR for P1: $^1$H NMR (400 MHz, METHANOL-d$_4$) δ ppm 0.92 (t, J=7.3 Hz, 3 H) 1.28-1.44 (m, 5 H) 1.51-1.66 (m, 2 H) 2.53 (ddd, J=11.9, 8.4, 7.0 Hz, 1 H) 2.61-2.76 (m, 1 H) 3.84 (dddd, J=9.5, 4.1, 1.9, 1.8 Hz, 1 H) 3.95 (dq, J=9.9, 7.1 Hz, 1 H) 4.02 (d, J=9.5 Hz, 1 H) 4.04-4.15 (m, 2 H) 4.30 (ddd, J=11.5, 6.6, 4.5 Hz, 1 H) 4.46 (ddd, J=11.8, 6.0, 2.0 Hz, 1 H) 4.49-4.57 (m, 2 H) 5.62 (d, J=8.0 Hz, 1 H) 6.11 (s, 1 H) 7.13-7.21 (m, 1 H) 7.21-7.30 (m, 2 H) 7.34 (d, J=7.5 Hz, 2 H) 7.54 (d, J=8.0 Hz, 1 H)

The optical rotation for P1 was measured using a Perkin Elmer 341 polarimeter. [α]$_D^{20}$ indicates the optical rotation measured with light at the wavelength of the D-line of sodium (589 nm) at a temperature of 20° C. The cell path length is 1 dm. Next to the actual value, the concentration and solvent of the solution which was used to measure the optical rotation are mentioned. [α]$_D^{20}$=+20.61° (589 nm, c 0.359 w/v %, ethanol, 20° C.)

Biological Example

Replicon Assay

The compound P1 was examined for activity in the inhibition of HCV-RNA replication in a cellular assay. The assay was used to demonstrate that compound P1 inhibited a HCV functional cellular replicating cell line, also known as HCV replicons. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy.

In essence, the method was as follows. The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an internal ribosome entry site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV genotype 1b. Continued culture of the replicon cells in the presence of G418

(neo$^R$) is dependent on the replication of the HCV-RNA. The stably transfected replicon cells that express HCV-RNA, which replicates autonomously and to high levels, encoding inter alia luciferase, were used for screening the antiviral compounds.

The replicon cells were plated in 384-well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for the test compound. The $EC_{50}$ value was then calculated, which value represents the amount of the compound required to decrease the level of detected luciferase activity by 50%, or more specifically, the ability of the genetically linked HCV replicon RNA to replicate.

The result is shown in table 1.

TABLE 1

| Compound | $EC_{50}$ (µM) (HCV) | $CC_{50}$ (µM) (Huh-7) |
|---|---|---|
| P1 | 2.51 | >98 |

Pharmaceutical Example

Film-Coated Tablet

"Active ingredient" as used throughout this example relates to a compound of formula (I), including a pharmaceutically acceptable salt thereof or a solvate thereof.

Preparation of Tablet Core

A mixture of 100 g of active ingredient, 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula I

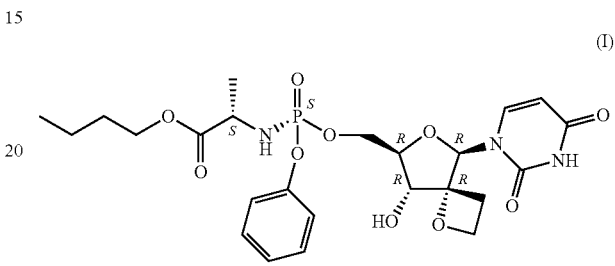

or a salt form or solvate thereof.

2. The compound of claim 1, wherein said compound is a salt.

3. The compound of claim 2 wherein the salt is a pharmaceutically acceptable salt.

4. The compound of claim 1, wherein said compound is a solvate.

5. The compound of claim 1 having a stereoisomeric excess of at least 80%.

6. The compound of claim 5 having a stereoisomeric excess of at least 90%.

7. The compound of claim 6 having a stereoisomeric excess of at least 94%.

8. A pharmaceutical composition comprising an anti-virally effective amount of the compound of claim 1, and a pharmaceutically acceptable carrier.

9. A method for treating a hepatitis C virus infection comprising contacting a cell with the compound of claim 1.

* * * * *